United States Patent
Donzier et al.

(10) Patent No.: US 10,527,751 B2
(45) Date of Patent: Jan. 7, 2020

(54) DOWNHOLE FLUID PROPERTIES OPTICAL ANALYSIS PROBE HAVING A REMOVABLE OPTICAL TIP

(71) Applicant: OPENFIELD, Versailles (FR)

(72) Inventors: Eric Donzier, Bercheres sur Vesgre (FR); Linda Abbassi, Montigny le Bretonneux (FR); Emmanuel Tavernier, Paris (FR)

(73) Assignee: OPENFIELD, Versailles (FR)

( * ) Notice: Subject to any disclaimer, the term of this patent is extended or adjusted under 35 U.S.C. 154(b) by 0 days.

(21) Appl. No.: 15/416,826

(22) Filed: Jan. 26, 2017

(65) Prior Publication Data

US 2017/0219737 A1    Aug. 3, 2017

(30) Foreign Application Priority Data

Feb. 1, 2016  (EP) ..................... 16305103

(51) Int. Cl.
  *G01V 8/16*   (2006.01)
  *G01N 21/85*  (2006.01)
  (Continued)

(52) U.S. Cl.
  CPC ............ *G01V 8/16* (2013.01); *E21B 17/1078* (2013.01); *E21B 47/011* (2013.01);
  (Continued)

(58) Field of Classification Search
  CPC .... G01V 8/16; G01N 21/8507; G02B 6/3624; E21B 17/1078; E21B 47/011; E21B 49/08
  (Continued)

(56) References Cited

U.S. PATENT DOCUMENTS 2,778,661 A * 1/1957 Leighton ................. F16L 23/10
                                                      285/110
3,068,400 A * 12/1962 Castel ................... E21B 47/026
                                                     192/116.5
(Continued)

FOREIGN PATENT DOCUMENTS

WO  WO 2015059380 A1 * 4/2015 ............... G01F 1/74
WO  WO2015059380 A1    4/2015

OTHER PUBLICATIONS

EP16305103, European Search Report, dated Jul. 4, 2016, Berlin.

*Primary Examiner* — David P Porta
*Assistant Examiner* — Blake C Riddick
(74) *Attorney, Agent, or Firm* — The Jansson Firm; Pehr B. Jansson

(57) ABSTRACT

A downhole fluid properties optical analysis probe (1) to analyze at least one property of a multiphase flow mixture (100) flowing in a hydrocarbon well (51) has an elongated cylindrical body shape. It comprises an optical tip (5) at one end of the elongated cylindrical body arranged to be in contact with the multiphase flow mixture (100). It further comprises an optical link (6) adapted for a connection with an electronics module (11) at another end of the elongated cylindrical body arranged to be separated from the multiphase flow mixture (100). The optical tip (5) is coupled to the optical link (6) through a removable and watertight coupling (7). The removable and watertight coupling comprises a first portion (9a) of a protective tube (9) resistant to downhole conditions, said first portion (9a) enclosing the optical link (6) and comprising at least one first ring bulge (22) close to a coupling interface (10), and a second portion (9b) of the protective tube (9) partially enclosing the optical tip (5) such as to let a distal end of the optical tip (5) in contact with the multiphase flow mixture (100), said second portion (9b) comprising at least one second ring bulge (23)

(Continued)

close to the coupling interface (10). It further comprises a coupling tube (24) surrounding facing ends of the first portion (9a) and the second portion (9b), said coupling tube (24) being adjusted in size to fit in between said first and second ring bulges (22, 23), and a coupling and protecting sheath (25) enclosing said first ring bulge (22), coupling tube (24) and second ring bulge (23) in a watertight manner.

10 Claims, 4 Drawing Sheets

(51) Int. Cl.
| | | |
|---|---|---|
| *G01N 21/47* | (2006.01) | |
| *E21B 47/10* | (2012.01) | |
| *G01N 21/64* | (2006.01) | |
| *E21B 17/10* | (2006.01) | |
| *E21B 47/01* | (2012.01) | |
| *E21B 49/08* | (2006.01) | |
| *G02B 6/44* | (2006.01) | |
| *G02B 6/36* | (2006.01) | |

(52) U.S. Cl.
CPC .......... *E21B 47/102* (2013.01); *E21B 49/08* (2013.01); *G01N 21/474* (2013.01); *G01N 21/645* (2013.01); *G01N 21/8507* (2013.01); *G01N 2021/4742* (2013.01); *G01N 2021/6484* (2013.01); *G01N 2021/8528* (2013.01); *G02B 6/3624* (2013.01); *G02B 6/4428* (2013.01)

(58) Field of Classification Search
USPC .......... 250/269.1, 256, 261, 262, 265, 268
See application file for complete search history.

(56) References Cited

U.S. PATENT DOCUMENTS

| | | | | |
|---|---|---|---|---|
| 3,740,155 A | * | 6/1973 | Keller | G01N 21/8507 356/246 |
| 3,956,760 A | * | 5/1976 | Edwards | G01F 23/24 340/620 |
| 4,577,109 A | * | 3/1986 | Hirschfeld | G01N 21/255 250/461.1 |
| 4,783,137 A | * | 11/1988 | Kosman | G02B 6/3825 250/227.24 |
| 4,975,187 A | * | 12/1990 | Espenan | B01D 63/02 210/321.89 |
| 5,309,626 A | * | 5/1994 | Tolino | G21C 13/028 29/281.1 |
| 5,743,343 A | * | 4/1998 | Heller | E21B 25/00 175/20 |
| 5,979,569 A | * | 11/1999 | Heller | E21B 25/00 166/169 |
| 6,937,188 B1 | * | 8/2005 | Saunders | H01Q 1/1257 342/359 |
| 2002/0009252 A1 | | 1/2002 | Maron et al. | |
| 2002/0179153 A1 | * | 12/2002 | Taylor | A62B 9/02 137/540 |
| 2003/0206026 A1 | * | 11/2003 | Diakonov | E21B 49/08 324/723 |
| 2004/0045350 A1 | * | 3/2004 | Jones | E21B 43/38 73/152.23 |
| 2007/0151727 A1 | * | 7/2007 | Tao | E21B 33/1216 166/250.1 |
| 2007/0171412 A1 | * | 7/2007 | Vannuffelen | G01J 3/0218 356/328 |
| 2008/0023328 A1 | * | 1/2008 | Jiang | E21B 47/10 204/407 |
| 2008/0207067 A1 | * | 8/2008 | Ricciuti | B63C 9/0005 441/11 |
| 2009/0014016 A1 | * | 1/2009 | Clifford | A61B 17/1764 128/898 |
| 2009/0178921 A1 | * | 7/2009 | Lawrence | E21B 47/01 204/400 |
| 2012/0043078 A1 | * | 2/2012 | Ziauddin | E21B 43/26 166/250.1 |
| 2013/0256133 A1 | * | 10/2013 | Lawrence | G01N 27/30 204/412 |
| 2014/0103203 A1 | * | 4/2014 | Tjhang | G01V 8/10 250/269.1 |
| 2015/0041118 A1 | * | 2/2015 | Chalumeau | C08K 5/12 166/242.2 |
| 2017/0298717 A1 | * | 10/2017 | Xiao | E21B 43/128 |

* cited by examiner

DOWNHOLE FLUID PROPERTIES OPTICAL ANALYSIS PROBE HAVING A REMOVABLE OPTICAL TIP

TECHNICAL FIELD

The invention relates to an optical analysis probe measuring downhole fluid properties comprising a removable and watertight coupling for the optical tip. Such an optical analysis probe may be integrated in a downhole measuring tool like a production logging tool used to analyze a multiphase fluid mixture flowing from a hydrocarbon bearing zone into a hydrocarbon well. Such probes and tools operate at downhole pressure and temperature conditions.

BACKGROUND

During the evaluation or production of a hydrocarbon well, it is necessary to monitor various parameters for example the relative volumetric flow rates of the different phases (e.g. oil, gas and water) of the multiphase fluid mixture flowing into the pipe of the well from the hydrocarbon bearing zones, and/or to identify the phases.

Optical analysis probes that are used within a downhole measuring tool operate in harsh environment, namely extreme conditions including high pressure from several hundred bars up to 2000 bars, high temperature up to 200° C., presence of corrosive fluids such as sulfuric acid, presence and contamination by solid particles such as scales, asphaltenes, sand particles, as well as multiphasic flow conditions (oil, gas, water). Furthermore, there is the high shocks environment associated to wireline or drilling or production logging operations.

During an evaluation operation or a production operation, the optical tip of the optical analysis probe may be damaged. Further, the technologies associated with the optical tip may evolve. There is a need to ease the replacement of the optical tip.

The document WO2015059380 describes an optical probe comprising an optical guide; a sleeve surrounding the optical guide; a tapered sapphire tip, with a circular base, mounted at one end of the optical guide; a linking tube into which the tip is inserted and from which the latter projects by the two ends thereof; and a cylindrical body into which the tube is inserted, one end of which is inserted into a sheath arranged at one end of the sleeve.

This optical probe describes a particular assembly for securing in a watertight manner the tapered sapphire tip to the probe. This results in a complex assembly that is difficult to dismantle in case a replacement of the tapered sapphire tip is necessary.

SUMMARY OF THE DISCLOSURE

It is an object of the invention to propose a downhole fluid properties optical analysis probe that overcomes one or more of the limitations of the existing devices. In particular, it is desirable to ease the replacement of the optical tip. More particularly, it is desirable to enable replacing the optical tip without having to dismantle the whole probe from a downhole measuring tool into which the probe is fitted.

According to one aspect, there is provided a downhole fluid properties optical analysis probe to analyze at least one property of a multiphase flow mixture flowing in a hydrocarbon well has an elongated cylindrical body shape. It comprises an optical tip at one end of the elongated cylindrical body arranged to be in contact with the multiphase flow mixture. It further comprises an optical link adapted for a connection with an electronics module at another end of the elongated cylindrical body arranged to be separated from the multiphase flow mixture. The optical tip is coupled to the optical link through a removable and watertight coupling. The removable and watertight coupling comprises a first portion of a protective tube resistant to downhole conditions, said first portion enclosing the optical link and comprising at least one first ring bulge close to a coupling interface, and a second portion of the protective tube partially enclosing the optical tip such as to let a distal end of the optical tip in contact with the multiphase flow mixture, said second portion comprising at least one second ring bulge close to the coupling interface. The removable and watertight coupling further comprises a coupling tube surrounding facing ends of the first portion and the second portion, said coupling tube being adjusted in size to fit in between said first and second ring bulges. The removable and watertight coupling further comprises a coupling and protecting sheath enclosing said first ring bulge, coupling tube and second ring bulge in a watertight manner.

The ring bulges may be chosen among the group comprising a ring bulge having a flat top, a ring bulge having a peaked top and a ring bulge having a rounded top.

Multiple consecutive first and second ring bulges may be positioned consecutively on each side of the coupling interface.

The coupling and protecting sheath may be made of a heat-shrink material.

The optical tip may be made of a sapphire rod being needle shaped and having an external diameter ranging from around 0.3 mm to around 1 mm, and the link is an optical fibers bundle.

An index gel layer may be positioned at the coupling interface between the optical fibers bundle and the other end of the optical tip.

According to a further aspect, there is provided a downhole fluid properties measuring tool comprising at least one downhole fluid properties analysis probe of the invention.

According to still a further aspect, there is provided a production logging tool comprising a central pressure-resistant rigid housing carrying external centralizers adapted for contact with a production pipe wall of a hydrocarbon well and at least one downhole fluid properties optical analysis probe of the invention secured on an inner face of the centralizers deploying arms such as to expose an optical tip to a multiphase fluid mixture flowing in the hydrocarbon well, an electronics module of the optical analysis probe being located into said housing, a protective tube extending from the electronics module to the optical tip through a pressure feedthrough into said housing.

According to still a further aspect, there is provided an optical tip of a downhole fluid properties optical analysis probe installation and replacement method comprising a step of plugging facing ends of the first portion and the second portion into the coupling tube, and coupling together the optical link and the optical tip; a step of sliding the coupling and protecting sheath from the optical tip towards the coupling zone so as to cover said first ring bulge, said coupling tube and said second ring bulge; and a step of heating around the coupling and protecting sheath at least up to a temperature that causes shrinking of a heat shrink/retractable material forming the coupling and protecting sheath such as to generate a sealing.

The installation and replacement method may further comprise a step of cutting and discarding the coupling and protecting sheath; a step of disconnecting and discarding the optical tip from the optical link; and repeating the plugging and coupling step, the sliding step and the heating step with a replacement optical tip.

With the invention, it is possible to replace the optical tip without having to dismantle the main parts of the probe, or without the necessity to dismantle the optical analysis probe from the downhole measuring tool. This is particularly advantageous in term of maintenance and in term of operation cost. Further, the removable coupling of the invention is particularly well adapted to the space constraints associated to downhole tools. Furthermore, the removable coupling of the invention is particularly well adapted to the pressure constraint of the harsh environment encountered in the hydrocarbon well. Furthermore, retrofitting downhole fluid properties optical analysis probe with new technology based optical tip (upgraded or improved optical tip) is rendered possible with the invention. Such a removable connection is particularly well adapted in the frame of oil & gas exploration and production industry where pressure constraints and size (small diameters) constraints are high.

Other advantages will become apparent from the hereinafter description of the invention.

BRIEF DESCRIPTION OF THE DRAWINGS

The present invention is illustrated by way of examples and not limited to the accompanying drawings, in which like references indicate similar elements.

DETAILED DESCRIPTION

The invention will be understood from the following description, in which reference is made to the accompanying drawings.

Figures 1, 2:
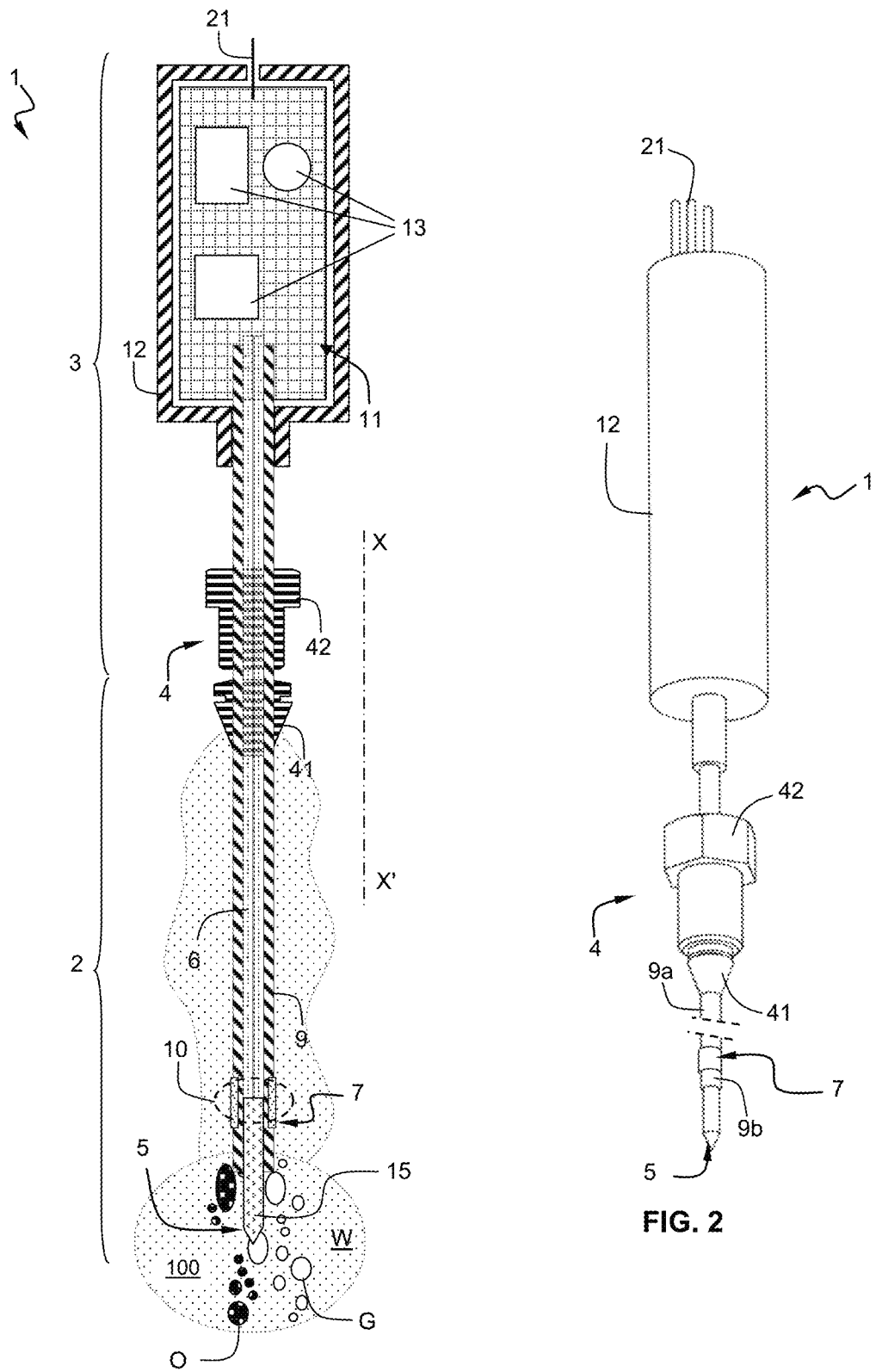
FIG. 1 is a partial cross-section view schematically illustrating an embodiment of f a downhole fluid properties optical analysis probe of the invention.
FIG. 2 is a perspective view of an assembled optical analysis probe of FIG. 1.

FIG. 1 is a partial cross-section view schematically illustrating a downhole fluid properties optical analysis probe 1.

The optical analysis probe 1 has the general shape of an elongated cylindrical body extending along the longitudinal axis XX'. The optical analysis probe 1 comprises a first portion 2 in contact with the well fluid 100 to be analyzed (i.e. in contact with harsh environments), and a second portion 3 separated from the fluid 100 to be analyzed (protected from harsh environments). A probe connector 4 separates the first portion 2 from the second portion 3.

In the first portion 2, an optical tip 5 is coupled to an optical link in the form of a single optical fiber (not depicted) or an optical fibers bundle 6 (e.g. optical fiber made of silica, fluoride glass, phosphate glass, chalcogenide glass, plastics, doped or not) that is inserted into a protective tube 9.

In a coupling zone 10, a removable and watertight coupling 7 is used to couple the optical tip 5 and the optical fibers bundle 6 in a removable and watertight manner. In this coupling zone 10, the protective tube 9 partially surrounds the optical tip 5 at the coupling zone 10, letting the distal part of the optical tip 5 in contact with the fluid 100 to be measured.

The second portion 3 comprises an electronic board 11 and a protective housing 12. The electronic board 11 forms an optoelectronics module comprising various components 13, e.g. a light source (e.g a LED or laser diode), at least one light detector (e.g. PIN photodiode), amplifiers, a measurement circuit, a processing module (e.g. microcontroller), and/or appropriate connectors. The electronic board 11 is coupled to the optical tip 5 through the optical link (i.e. the optical fibers bundle 6). The electronic board 11 is also connected to cables 21 that may comprise power input cable and a digital data output cable.

The optical tip 5 is a sapphire rod having a needle shape. The external diameter of the sapphire rod ranges from about 0.3 mm to about 1 mm. The sapphire material has a particular robustness in corrosive environments. The needle shape has the property of fast piercing liquid interfaces and self cleaning in multiphasic conditions. At least droplets of fluids rarely stick on such a tip. The angle at the end of the tip may be any angle from 30° to 90°. Alternatively, the tip may be bi-conical thus having two angles, or any other shape such as a cone with an hemispherical or rounded end or any combination of conical and spherical.

Figure 6A:
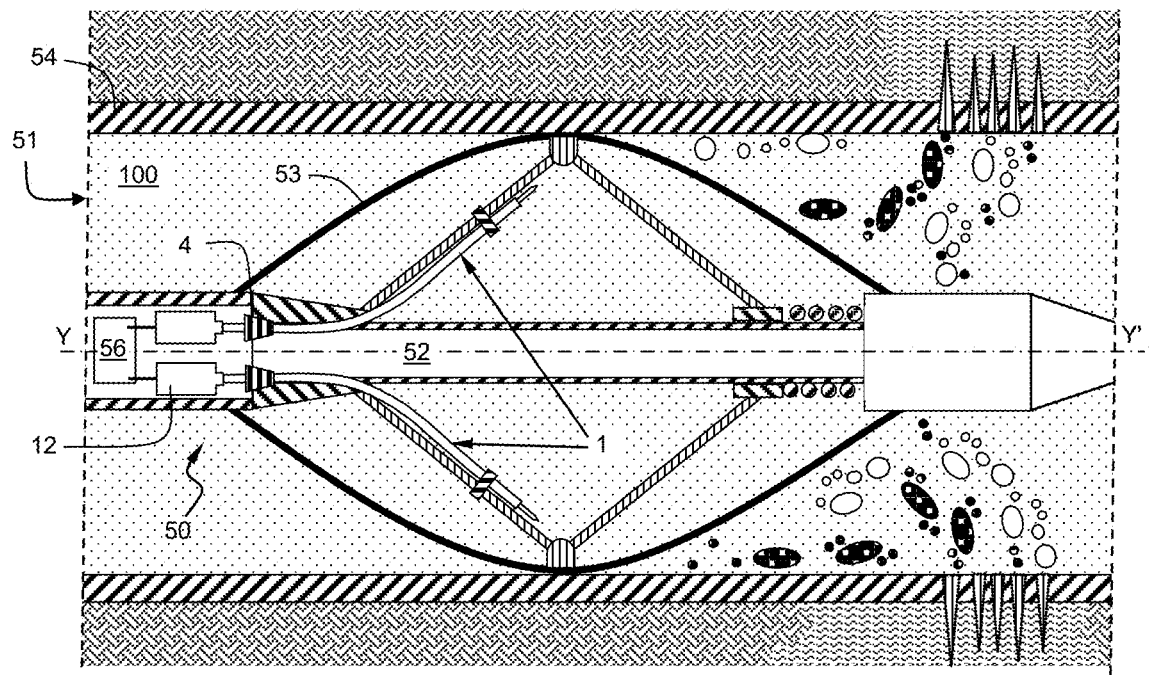
FIGS. 6a and 6b are a cross-section view and a perspective view of a downhole measuring tool like a production logging tool, respectively.
Figure 6B:
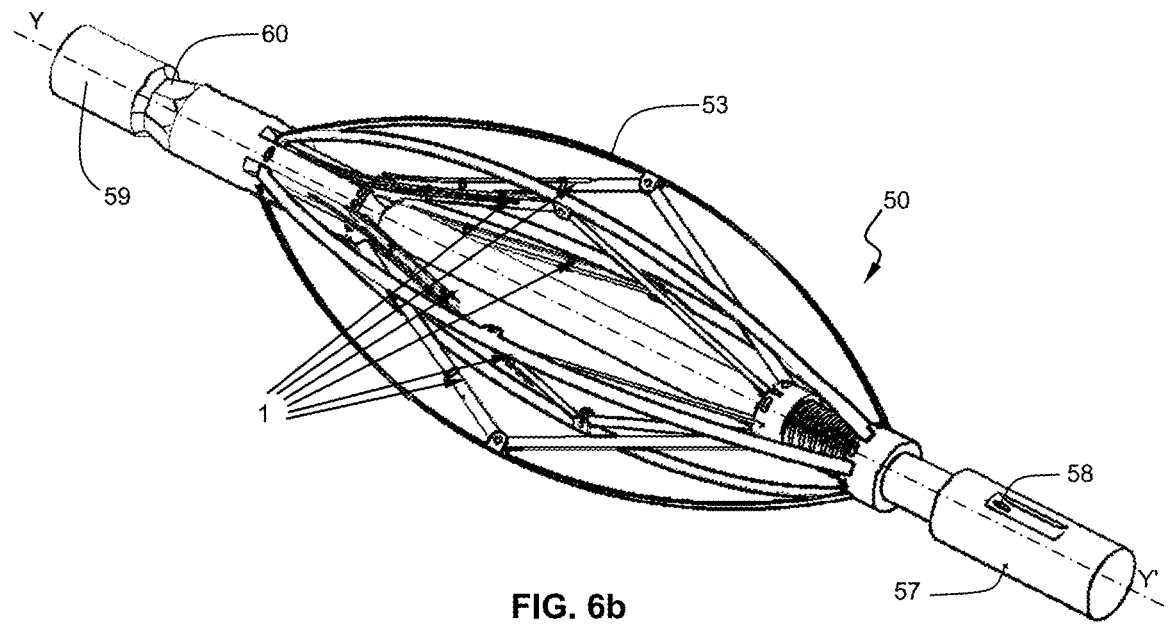

The protective tube 9 is made of metal or alloy. Metal or alloy offering high strength and high chemical resistance such as Inconel can suitably be used. The protective tube 9 is used to mechanically maintain the sapphire rod optical tip 5 and the optical fiber bundle 6, to protect the optical fiber bundle 6 from fluids 100, and to hold the probe connector 4. The sealing of the protective tube 9 against the optical tip 5 by a removable and watertight coupling 7 in a coupling zone 10 between the optical fibers bundle 6 and the optical tip 5 in order to avoid penetration of fluid towards the interface (or contact) zone between the optical fibers bundle 6 end and the back face of the sapphire optical tip 5 and the second portion 3 will be explained in details hereinafter. As a particular example, the protective tube 9 has an external diameter of 0.5 mm to 3 mm, and is ranging from a few centimeters to a few tens of centimeters long (e.g. 25.4 cm/10 inches). Therefore, the protective tube 9 has bending capacity that enables precisely positioning the optical tip 5 relatively to the second portion 3, in particular to position the optical tip 5 at the place where measurements are to be performed (such a capacity is illustrated in FIGS. 6a and 6b).

FIG. 2 is a perspective view of an assembled optical analysis probe 1. The probe connector 4 may slide onto the protective tube 9 and is sealed against the protective tube 9 once in place. The probe connector 4 is adapted to be connected by a screw nut type connection to a hole of a housing of a tool sub-module as depicted in FIGS. 6a and 6b. The screw nut connection may be a conical synthetic rubber/fluoropolymer elastomer ferule 41 (metal-elastomer seal), or a conical metal ferrules 41 (metal-metal seal). For example, synthetic rubber/fluoropolymer elastomer may be Viton fluoroelastomers a registered trademark of DuPont Performance Elastomers L.L.C. A high pressure seal connection is obtained when the screw 42 associated with the conical ferule 41 both slidingly coupled to the protective tube 9 is appropriately screwed into a threaded hole. Other waterproof and high pressure connections may be appropriate, for example a screw nut connection including an O-ring.

As a further alternative the connection may be a welded connection, the protective tube 9 being welded to the hole of the housing of the tool sub-module.

Figure 3A:
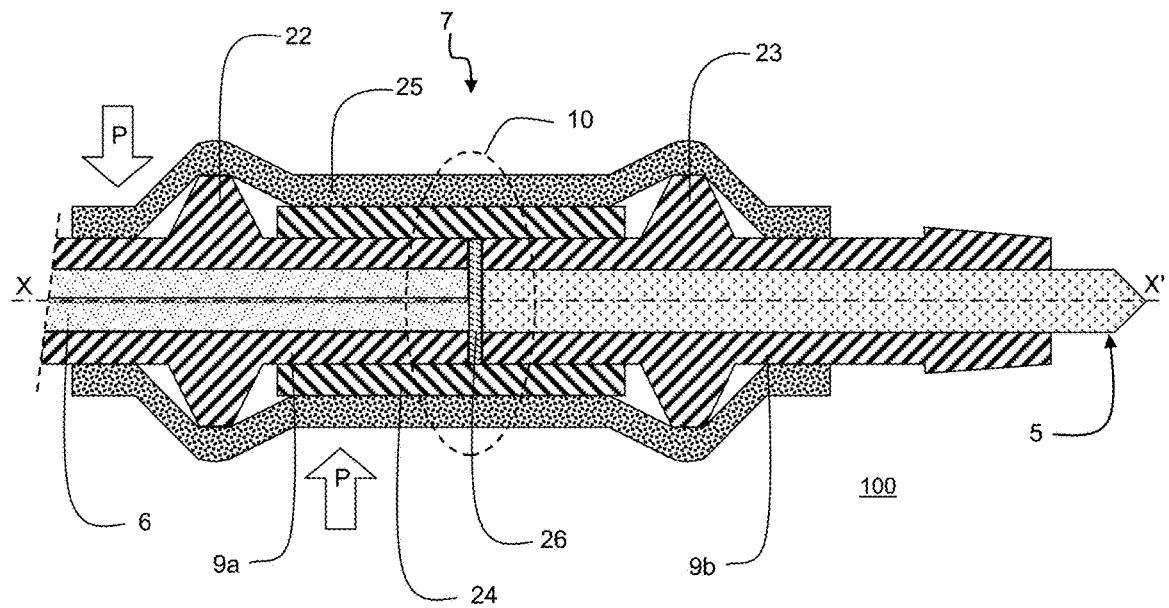
FIGS. 3a and 3b are enlarged cross-section views along the longitudinal axis of the optical analysis probe showing two embodiments of a removable and watertight coupling of the optical analysis probe of FIG. 1.
Figure 3B:
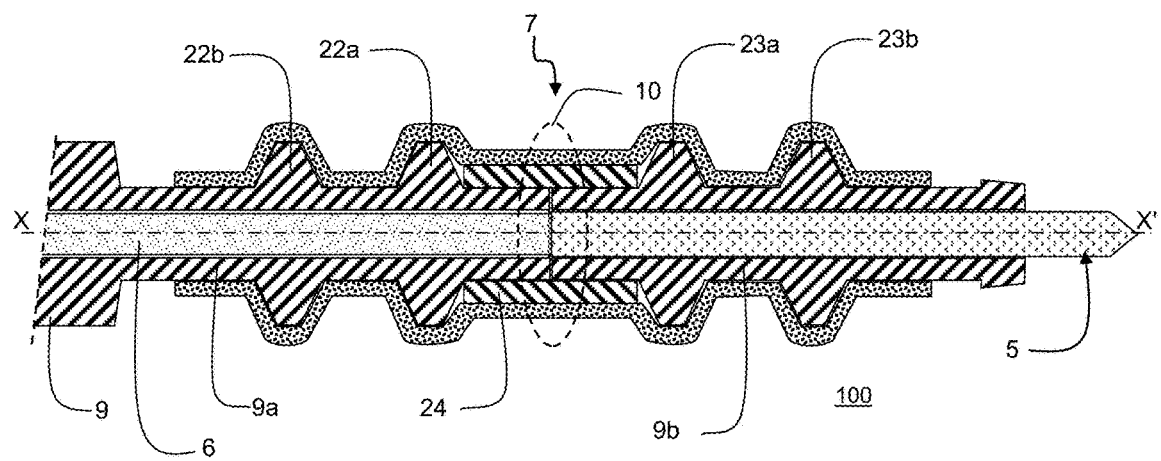

FIGS. 3a and 3b are enlarged cross-section views along the longitudinal axis XX' of the optical analysis probe 1 showing two embodiments of the removable and watertight coupling 7 of the optical analysis probe. The removable and watertight coupling 7 enables improving the sealing in order to avoid penetration of fluid towards the optical link (single optical fiber or optical fibers bundle 6) and the second portion 3. Additionally, the removable and watertight coupling 7 enables changing the optical tip 5 from the optical analysis probe 1 in case the optical tip 5 is damaged or special probes design are desired for particular operations. The protective tube 9 comprises a first portion 9a and a second portion 9b. The first portion 9a of the protective tube 9 encloses the optical link and comprises a first ring bulge 22 close to the coupling zone 10. The second portion 9b of the protective tube 9 partially encloses the optical tip 5 and comprises a second ring bulge 23 close to the coupling zone 10. The facing ends of the first portion 9a and the second portion 9b are surrounded by a coupling tube 24 that is adjusted in size to fit in between the first ring bulge 22 and the second ring bulge 23 and allows a tight contact between the optical fibers bundle and the sapphire rod tip. A coupling and protecting sheath 25 encloses the first ring bulge 22, the coupling tube 24 and the second ring bulge 23. The protective tube 9, the ring bulges 22, 23, the coupling tube 24 and the coupling and protecting sheath 25 have all a general cylindrical shape and are co-axial (of longitudinal axis XX'). The protective tube 9, 9a, 9b, the ring bulges 22, 23 and the coupling tube can be made of metal or alloy offering high strength and high chemical resistance (e.g. Inconel). The coupling and protecting sheath 25 can be made of a heat shrink/retractable polymer, for example a heat retractable synthetic rubber/fluoropolymer elastomer. Other heat shrink/retractable material may be suitable provided that the material is non-porous and/or provided a sufficient water-tightness. During the installation of the removable and watertight coupling 7, the coupling and protecting sheath 25 is heated in order to apply it onto the bulges and the coupling tube 24. Further, during use, the effect of pressure P of the fluid 100 to be measured tends to apply the sheath 25 onto the bulges and the coupling tube 24 thus additionally sealing the protective tube 9, 9a, 9b against the optical tip 5 and against the optical link. This is particularly effective in avoiding the penetration of fluids towards the optical link and the second portion 3.

The ring bulges 22, 23 are manufactured by machined thinning the protective tube 9 in the first and second portions 9a, 9b (this is best to be seen in FIG. 3b). Therefore, the top surface of the ring bulges is flush with the external surface of the protective tube 9. The depth of the machining and thus the height of the bulges is ranging from 10 µm to 200 µm. The coupling tube 24 has an internal diameter slightly above the thinned first and second portions 9a, 9b so as to slide on it and an external diameter inferior to the ring bulges. The coupling and protecting sheath 25 has a few µm thickness. Therefore, once shrunk in place, except above the ring bulges, the coupling and protecting sheath 25 is below or flush with the non-machined part of the protective tube 9. Thus, with the invention, a removable and watertight coupling 7 for the optical tip 5 is achieved that is light and miniaturized without disturbing the flow of fluid around the optical tip. It can be easily integrated in complex tools or infrastructure element.

The embodiment of FIG. 3b differs from the embodiment of FIG. 3a in that several ring bulges are positioned in series in order to create additional barriers to the penetration of fluids and, therefore, providing a further sealing in harsh environment. As an example, FIG. 3b depicts an embodiment comprising two first ring bulges 22 associated with the first portion 9a and two second ring bulges 23 associated with the second portion 9b (i.e. positioned on each side of the coupling zone 10 so as to tightly seals the coupling interface).

The optical tip 5 may be directly coupled to the optical fibers bundle 6 (as depicted in FIG. 3b). Optionally, an index gel layer 26 may be positioned at the interface of these optical elements (as depicted in FIG. 3a).

Figure 4A:
FIGS. 4a, 4b and 4c show various embodiments of ring bulge.
Figure 4B:
Figure 4C:

FIGS. 4a, 4b and 4c schematically depict various shapes of ring bulge (first and/or second ring bulge 22, 23, respectively), namely a ring bulge having a flat top, a ring bulge having a peaked top and a ring bulge having a rounded top, respectively. Such shapes may be combined, meaning that the shape of the ring bulge associated to the first portion 9a is not necessarily the same as the ring bulge associated to the second portion 9b.

The principle of operation of the optical analysis probe is not germane to the present invention and will therefore not be described in details. As an example, the operation of the optical analysis probe of the optical type is described in EP16305013.1. When the optical tip of the optical analysis probe 1 is immerged into a multiphase fluid mixture 100, it can be used to estimate relative volumetric flow rates of different phases (e.g. oil O, gas G and water W). The optical analysis probe uses the fluid reflectance to derive the gas hold-up, and the fluid fluorescence to derive the oil hold-up. In particular, the optoelectronics module (components 13 of the electronic board 11) controls the emission of a light signal in a determined wavelength range towards the optical tip 5 through the optical fibers bundle 6. When a gas bubble G, respectively an oil bubble O is present at the tip 5, a light signal is collected at the optical tip 5 and directed towards a light detector (components 13 of the electronic board 11) through the optical fibers bundle 6, said light signals being representative of the occurrence of a reflectance, respectively a fluorescence effect. The optical signals are transformed in electrical signals that are amplified and provided to the processing module (components 13 of the electronic board 11). When the corresponding electrical signals are above a mean level signal, a gas bubble G, respectively an oil bubble O is detected. The duration estimation of the presence of the gas bubble G, respectively an oil bubble O at the optical tip 5 is used to estimate the relative volumetric flow rates of the different phases.

Figure 5:
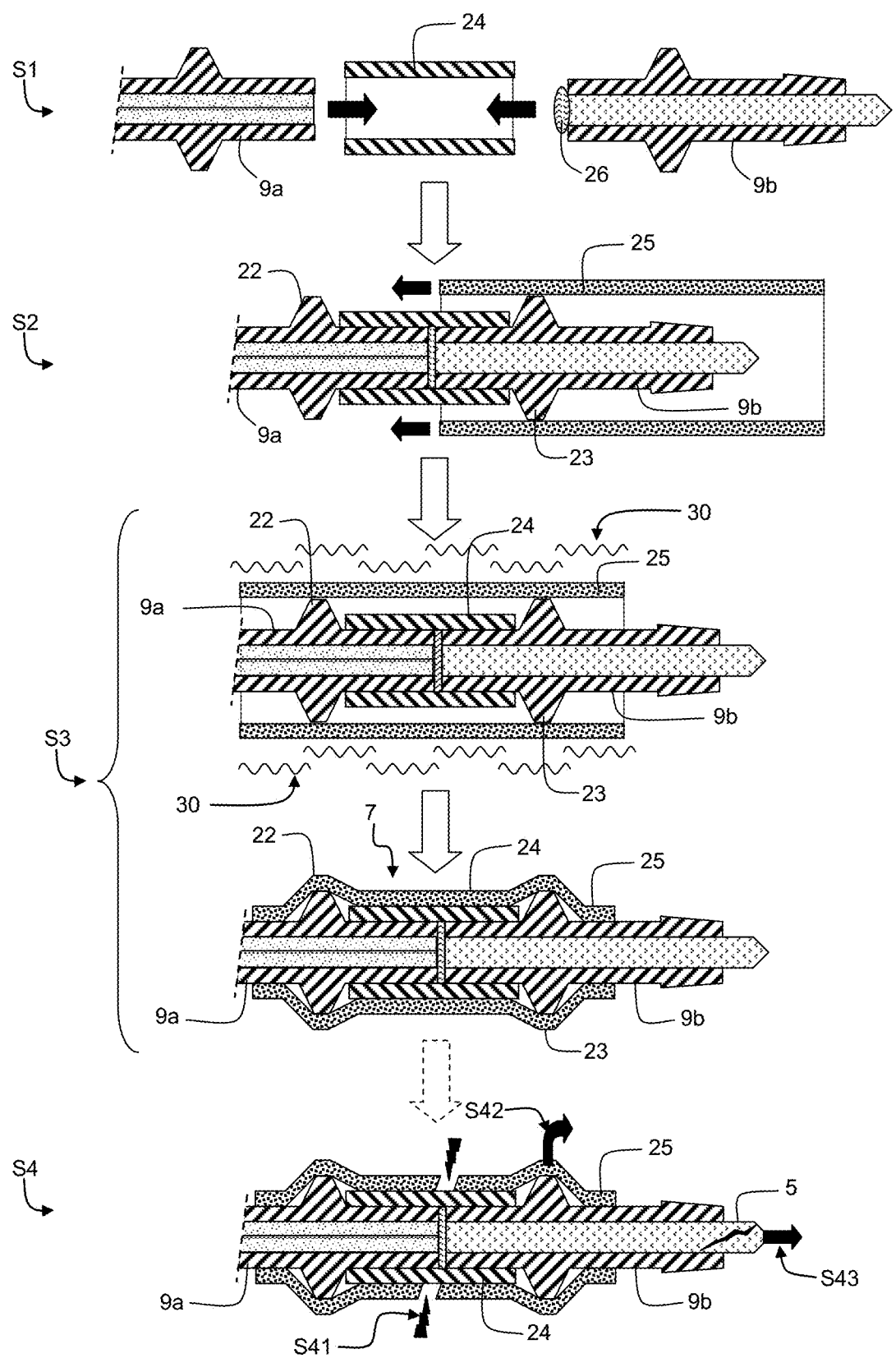
FIG. 5 schematically illustrates a optical tip coupling and replacement method of the optical analysis probe of FIG. 1.

FIG. 5 schematically illustrates an optical tip coupling and replacement method of the downhole fluid properties optical analysis probe of FIG. 1. In the following description, it is understood that some elements of the optical analysis probe are pre-assembled, namely, the second portion 3 of the optical analysis probe, the optical link (single optical fiber or optical fibers bundle 6) and the first portion 9a of the protective tube 9 opposite the tip side; and the optical tip 5 and the second portion 9b of the protective tube 9 at the tip side.

In a first step S1, the facing ends of the first portion 9a and the second portion 9b are plug into the coupling tube 24. The optical link and the optical tip are coupled together, either by direct coupling or through an index gel layer 26.

In a second step S2, the coupling and protecting sheath 25 is slid from the optical tip 5 towards the coupling zone 10 so as to cover the first ring bulge 22, the coupling tube 24 and the second ring bulge 23. The diameter of the coupling and protecting sheath 25 is slightly superior to the diameter of the ring bulges 22, 23 so as to slide easily on the bulges.

In a third step S3, the coupling zone 10 around the coupling and protecting sheath 25 is heated at least up to a temperature that causes the shrinking of the heat shrink/retractable material forming the coupling and protecting sheath 25. The coupling and protecting sheath 25 is thus applied onto the first and second portions 9a, 9b, the bulges 22, 23 and the coupling tube 24. This seals the protective tube 9, 9a, 9b against the optical tip 5 and against the optical link 6.

In case the optical tip 5 is damaged and needs to be repaired, or needs to be retrofitted (i.e. replaced by an evolved version of the optical tip), in a fourth step S4, the coupling and protecting sheath 25 is cut all along the length of the sheath (according to the longitudinal axis XX') S41 and discarded S42, and the optical tip 5 can be disconnected from the optical link 6 and discarded S43. Then, the above steps S1 to S3 are repeated with a replacement optical tip 5.

Thus, changing the optical tip by another one, is a simple operation that only implies to cut the coupling and protecting sheath 25 and slide the coupling tube. After the optical tip is replaced, a new coupling and protecting sheath is simply appropriately positioned to replace the destroyed one.

FIGS. 6a and 6b are a cross-section view and a perspective view of a downhole measuring tool like a production logging tool unit 50 adapted for operation in a hydrocarbon producing well 51, respectively.

Multiple downhole fluid properties optical analysis probes 1 are mounted in the production logging tool unit 50 used for production evaluation of hydrocarbon wells. Generally, the production logging tool unit 50 also comprises other kinds of sensor/probe like pressure, temperature and flow sensors. The production logging tool unit 50 has a central pressure-resistant rigid housing 52 that carries external centralizers 53 adapted for contact with the production pipe walls 54 of the well 51. Multiple downhole fluid properties optical analysis probes 1 (first portion 2) as described above are secured on the inner face of the centralizers 53 deploying arms, for example by attaching the protective tube 9 such as to expose the optical tip 5 to the multiphase fluid mixture 100. The downhole fluid properties optical analysis probes 1 may be located at angularly distributed locations with respect to the central axis YY' of the production logging tool unit 50. Such a distributed probes arrangement solves the issue of measurement representativeness in inhomogeneous fluid flow as multiple measurements by multiple local probes become representative of the overall fluid flowing into the conduit of the well 51. Each downhole fluid properties optical analysis probe 1 (second portion 3) are connected through a pressure feedthrough, for example the probe connector 4 into the housing 52 such that the electronic board 11 and the protective housing 12 are located inside the housing 52 of the production logging tool 50. The electronic board 11 is connected to a power and processing circuit 56 that delivers power to each downhole fluid properties optical analysis probe 1 and receives local downhole fluid properties measured by each downhole fluid properties optical analysis probe 1. The production logging tool unit depicted in FIG. 6b may be connected endwise to various sections carrying other types of fluid sensors such as pressure sensors 57, temperature sensors 58, flowrate sensors 59 and imager 60.

Multiple production logging tool units may assembled together in a string (not shown). Using at least two production logging tool units allows cross correlation measurement on fluid holdups. Hydrocarbon wells production fluctuates with time, generating slugs and/or clouds of droplets or bubbles which propagate along the well. Measuring those corresponding variations using the optical probes of the invention installed in at least two units allows deducing dispersed phase velocity and interpreting critical production parameter such as water, oil, gas entries in specific well sections.

The drawings and their description hereinbefore illustrate rather than limit the invention.

It should be appreciated that embodiments of the production logging tool according to the present invention are not limited to the embodiment showing horizontal hydrocarbon well bore, the invention being also applicable whatever the configuration of the well bore, namely vertical, inclined or a combination of vertical, inclined and/or horizontal portions, cased or uncased. Also, the downhole fluid properties optical analysis probe of the invention is not limited to an application into a production logging tool, but can be easily adapted to various applications into analysis tools operating at downhole pressure and temperature conditions, e.g. a downhole fluid analysis tool, a wireline tool, a logging while drilling tool, a formation tester. Further, the number of optical fiber in the optical link is not limited to the depicted embodiment; the optical link may comprise one, two, three or more optical fibers. Furthermore, the shape of the optical tip is not limited to the depicted embodiment; various other kinds of tip shape have been suggested in the above description.

The invention claimed is:

1. A downhole fluid properties optical analysis probe to analyze at least one property of a multiphase flow mixture flowing in a hydrocarbon well has an elongated cylindrical body shape and comprises:
   an optical tip at one end of the elongated cylindrical body arranged to be in contact with the multiphase flow mixture;
   an optical link adapted for a connection with an electronics module at another end of the elongated cylindrical body arranged to be separated from the multiphase flow mixture, said electronics module comprising a light source;
   wherein the optical tip is coupled to the optical link through a removable and watertight coupling being welds free and O-ring seal free, the removable and watertight coupling comprising:
   a first portion of a protective tube resistant to downhole conditions, said first portion enclosing the optical link and comprising at least one first ring bulge close to a coupling zone;
   a second portion of the protective tube partially enclosing the optical tip such as to let a distal end of the optical tip in contact with the multiphase flow mixture, said second portion comprising at least one second ring bulge close to the coupling zone;
   a coupling tube surrounding facing ends of the first portion and the second portion, said coupling tube being adjusted in size to fit in between said first and second ring bulges; and
   a coupling and protecting sheath enclosing said first ring bulge, coupling tube and second ring bulge in a watertight manner, said sheath being configured so that during use, the effect of pressure of the multiphase flow mixture flowing in the hydrocarbon well tends to apply said sheath onto the first and second ring bulges and the coupling tube such as to additionally seal the protective tube against the optical tip and against the optical link.

2. The optical analysis probe of claim 1, wherein the ring bulges are chosen among the group comprising a ring bulge having a flat top, a ring bulge having a peaked top and a ring bulge having a rounded top.

3. The optical analysis probe of claim 1, wherein multiple consecutive first and second ring bulges are positioned consecutively around the coupling zone.

4. The optical analysis probe of claim 1, wherein the coupling and protecting sheath is made of a heat-shrink material.

5. The optical analysis probe of claim 1, wherein the optical tip is made of a sapphire rod being needle shaped and having an external diameter ranging from 0.3 mm to 1 mm, and the link is an optical fibers bundle.

6. The optical analysis probe of claim 5, wherein an index gel layer is positioned at the coupling zone between the optical fibers bundle and the other end of the optical tip.

7. A downhole fluid properties measuring tool comprising at least one downhole fluid properties optical analysis probe in accordance with claim 1.

8. A production logging tool comprising a central pressure-resistant rigid housing carrying external centralizers adapted for contact with a production pipe wall of a hydrocarbon well and at least one downhole fluid properties optical analysis probe in accordance with claim 1 secured on an inner face of the centralizers deploying arms such as to expose an optical tip to a multiphase fluid mixture flowing in the hydrocarbon well, an electronics module of the optical analysis probe being located into said housing, a protective tube extending from the electronics module to the optical tip through a pressure feedthrough into said housing.

9. An optical tip of a downhole fluid properties optical analysis probe installation method, said optical analysis probe comprising an optical tip partially mounted into a protective tube resistant to downhole conditions letting a distal end of the optical tip in contact with a multiphase flow mixture and coupled to an optical link mounted into the protective tube at the other end of the optical tip through a removable and watertight coupling being welds free and O-ring seal free, the protective tube comprising a first portion and a second portion, the first portion enclosing the optical link and comprising at least one first ring bulge close to a coupling zone, the second portion partially enclosing the optical tip and comprising at least one second ring bulge close to the coupling zone, wherein facing ends of the first portion and the second portion are surrounded by a coupling tube that is adjusted in size to fit in between said first and second ring bulges, and wherein a coupling and protecting sheath encloses said first ring bulge, said coupling tube and said second ring bulge, said sheath being configured so that during use, the effect of pressure of the multiphase flow mixture flowing in the hydrocarbon well tends to apply said sheath onto the first and second ring bulges and the coupling tube such as to additionally seal the protective tube against the optical tip and against the optical link, the installation method comprising:
- plugging facing ends of the first portion and the second portion into the coupling tube, and coupling together the optical link and the optical tip;
- sliding the coupling and protecting sheath from the optical tip towards the coupling zone so as to cover said first ring bulge, said coupling tube and said second ring bulge; and
- heating around the coupling and protecting sheath at least up to a temperature that causes shrinking of a heat shrink/retractable material forming the coupling and protecting sheath such as to generate a sealing.

10. An optical tip of a downhole fluid properties optical analysis probe replacement method, said optical analysis probe comprising an optical tip partially mounted into a protective tube resistant to downhole conditions letting a distal end of the optical tip in contact with a multiphase flow mixture and coupled to an optical link mounted into the protective tube at the other end of the optical tip through a removable and watertight coupling being welds free and O-ring seal free, the protective tube comprising a first portion and a second portion, the first portion enclosing the optical link and comprising at least one first ring bulge close to a coupling zone, the second portion partially enclosing the optical tip and comprising at least one second ring bulge close to the coupling zone, wherein facing ends of the first portion and the second portion are surrounded by a coupling tube that is adjusted in size to fit in between said first and second ring bulges, and wherein a coupling and protecting sheath encloses said first ring bulge, said coupling tube and said second ring bulge, said sheath being configured so that during use, the effect of pressure of the multiphase flow mixture flowing in the hydrocarbon well tends to apply said sheath onto the first and second ring bulges and the coupling tube such as to additionally seal the protective tube against the optical tip and against the optical link, the replacement method comprising:
- cutting and discarding the coupling and protecting sheath;
- disconnecting and discarding the optical tip from the optical link;
- plugging facing ends of the first portion and the second portion into the coupling tube, and coupling together the optical link and a replacement optical tip;
- sliding a replacement coupling and protecting sheath from the replacement optical tip towards the coupling zone so as to cover said first ring bulge, said coupling tube and said second ring bulge; and
- heating around the replacement coupling and protecting sheath at least up to a temperature that causes shrinking of a heat shrink/retractable material forming the replacement coupling and protecting sheath such as to generate a sealing.

* * * * *